(12) United States Patent
Liu et al.

(10) Patent No.: US 12,272,430 B2
(45) Date of Patent: Apr. 8, 2025

(54) BASE MUTATION DETECTION METHOD AND APPARATUS BASED ON SEQUENCING DATA, AND STORAGE MEDIUM

(71) Applicant: BGI GENOMICS CO., LTD., Guangdong (CN)

(72) Inventors: Siyang Liu, Guangdong (CN); Shujia Huang, Guangdong (CN); Xin Jin, Guangdong (CN)

(73) Assignee: BGI GENOMICS CO., LTD., Shenzhen (CN)

( * ) Notice: Subject to any disclaimer, the term of this patent is extended or adjusted under 35 U.S.C. 154(b) by 820 days.

(21) Appl. No.: 17/522,920

(22) Filed: Nov. 10, 2021

(65) Prior Publication Data

US 2022/0068437 A1 Mar. 3, 2022

Related U.S. Application Data

(63) Continuation of application No. PCT/CN2019/086972, filed on May 15, 2019.

(51) Int. Cl.
*G16B 40/00* (2019.01)
*G06N 7/01* (2023.01)
*G16B 20/20* (2019.01)

(52) U.S. Cl.
CPC .............. *G16B 40/00* (2019.02); *G06N 7/01* (2023.01); *G16B 20/20* (2019.02)

(58) Field of Classification Search
CPC .................................................. G16B 40/00
(Continued)

(56) References Cited

U.S. PATENT DOCUMENTS

2011/0246409 A1* 10/2011 Mitra ................. G06F 17/18 702/179
2014/0143188 A1* 5/2014 Mackey ................. G06N 7/01 706/12

(Continued)

FOREIGN PATENT DOCUMENTS

CN 106570350 A 4/2017
CN 107491666 A 12/2017
(Continued)

OTHER PUBLICATIONS

Bingshan Li et al., "A Likelihood-Based Framework for Variant Calling and De Novo Mutation Detection in Families", PLOS Genetics, vol. 8, Issue 10, p. e1002944, Oct. 4, 2012, DOI: 10.1371/journal.pgen.1002944 (Year: 2012).*

(Continued)

*Primary Examiner* — Reza Nabi
(74) *Attorney, Agent, or Firm* — Duane Morris LLP (57) ABSTRACT

Provided is a base mutation detection method, which includes: determining an initial frequency of sequencing data of samples being a specific base at an interested locus; calculating, based on the initial frequency, an expected value of each sample being the specific base at the interested locus; updating the initial frequency of the sequencing data of the samples being the specific base at the interested locus; further calculating the expected value of each sample being the specific base at the interested locus, further updating the initial frequency of the sequencing data of the samples being the specific base at the interested locus, and repeating the foregoing iteration until the expected value of each sample being the specific base at the interested locus converges; and determining, based on each converging expected value, a base mutation type and a mutation confidence at the interested locus of each sample.

15 Claims, 5 Drawing Sheets

(58) Field of Classification Search
USPC .......................................................... 706/52
See application file for complete search history.

(56) References Cited

U.S. PATENT DOCUMENTS

| | | | | |
|---|---|---|---|---|
| 2017/0321284 | A1* | 11/2017 | McCarroll | C12Q 1/6883 |
| 2019/0367978 | A1* | 12/2019 | West | C12Q 1/6874 |
| 2019/0382842 | A1* | 12/2019 | Meurs | G01N 33/6893 |
| 2020/0402610 | A1* | 12/2020 | Burke | G16B 30/10 |
| 2021/0020265 | A1* | 1/2021 | Burke | G16B 20/10 |
| 2021/0246510 | A1* | 8/2021 | West | C12Q 1/6886 |
| 2022/0068437 | A1* | 3/2022 | Liu | G06N 7/01 |

FOREIGN PATENT DOCUMENTS

| | | |
|---|---|---|
| CN | 108733975 A | 11/2018 |
| CN | 113795886 B | 12/2021 |
| WO | 2017115741 A1 | 7/2017 |

OTHER PUBLICATIONS

Shiraishi et al., "An empirical Bayesian framework for somatic mutation detection from cancer genome sequencing data", Nucleic Acids Res. Feb. 10, 2013; 41:e89 (Year: 2013).*

Heng Li, "A statistical framework for SNP Calling, mutation discovery, association mapping and population genetical parameter estimation from sequencing data", Bioinformatics, vol. 27, No. 21, Sep. 8, 2011, pp. 2987-2993, doi: 10.1093/bioinformatics/btr509 (Year: 2011).*

Bingshan Li et al., "A Likelihood-Based Framework for Variant Calling and De Novo Mutation Detection in Families", PLOS Genetics, vol. 8, Issue 10, p. e1002944, Oct. 4, 2012,DOI: 10.1371/journal.pgen.1002944.

Heng Li, "A statistical framework for SNP Calling, mutation discovery, association mapping and population genetical parameter estimation from sequencing data", Bioinformatics, vol. 27, No. 21, 2011, pp. 2987-2993,doi: 10.1093/bioinformatics/btr509.

Saharon Rosset et al., "Maximum-Likelihood Estimation of Site-Specific Mutation Rates in Human Mitochondrial DNA From Partial Phylogenetic Classification", Genetics, 180: 1511-1524 (Nov. 2008), pp. 1511-1514, DOI: 10.1534/genetics.108.091116.

Xing Hua, "Study on Statistical Methods for Cancer Genome Sequencing Data", Chinese Doctoral Dissertations Full-Text Database (Electronic Journals), No. 01, Jan. 15, 2013 (Jan. 15, 2013), A006-18, see sections 2.1, 2.2 and 2.3.

The extended European search report in counterpart European Application No. 19928972.9, dated Apr. 4, 2022.

First Substantive Examination Report in Saudi Arabia Patent Application No. 521430823, dated Dec. 14, 2022.

* cited by examiner

BASE MUTATION DETECTION METHOD AND APPARATUS BASED ON SEQUENCING DATA, AND STORAGE MEDIUM

CROSS-REFERENCE TO RELATED APPLICATIONS

This application is a continuation of International Application No. PCT/CN2019/086972, filed on May 15, 2019, which is incorporated herein by reference in its entirety.

FIELD

Embodiments of the present disclosure relate to technology of gene mutation detection, for example, relate to base mutation detection method and device based on sequencing data, and a storage medium.

BACKGROUND

With the advance and commercialization of the next-generation sequencing technology since 2008, sequencing data has continued to grow, and algorithms for multiple downstream applications based on the sequencing data have also been actively developed. One type of algorithms having prospects for broad applications is referred to as a base mutation detection method based on sequencing data. Genome variation include single nucleotide variation (base mutation), small insertions and deletions, and structural variations. Different genomic mutations have respective different detection algorithms. The present disclosure is directed to the base mutation detection. For the base mutation detection in the next-generation sequencing technology, there have been relatively stable open-source algorithms, such as the Genome Analysis ToolKit (GATK).

However, the algorithms of the base mutation detection in the related art still have the following main defects: first, they cannot detect tri-allelic and tetra-allelic mutation sites; and second, they are not suitable for scenarios of low sequencing depth and large sample data. For example, due to issues of memory and speed, the algorithms of the base mutation detection cannot even stably analyze data of more than 50,000 samples. Non-invasive prenatal testing is a type of whole-genome and ultra-low depth sequencing, with an average sequencing depth as low as 0.06× and a genome coverage rate of about 6%. Although the sequencing depth is very low, a large amount of non-invasive prenatal sequencing data, such as sequencing data of one hundred thousand, one million or even ten million cases, thereby constituting an excellent raw data set for mutation detection. In addition, the non-invasive prenatal sequencing data of about 7.2 million people has been accumulated all over the world. The population-specific mutation spectrum obtained based on the accumulated population genome sequencing data plays an important guiding role for disease research and drug development.

In such a scenario with ultra-large-scale samples but with low sequencing depth, the algorithms of the base mutation detection known in related art no longer work. Therefore, it appears very necessary to develop a new algorithm for base mutation detection, which is adapted to the above application scenario.

SUMMARY

The present disclosure discloses a base mutation detection method, base mutation detection apparatus and storage medium based on sequencing data. Through the method, base mutation detection can be achieved for the sequencing data with a low sequencing depth and a large amount of data.

The embodiments of the present disclosure disclose a base mutation detection method based on sequencing data, including: determining an initial frequency of sequencing data of a plurality of samples to be detected being a specific base at an interested locus; calculating, based on the initial frequency, an expected value of each of the plurality of samples to be detected being the specific base at the interested locus; updating, by using each expected value, the initial frequency of the sequencing data of the plurality of samples to be detected being the specific base at the interested locus; further calculating, by using the updated initial frequency, the expected value of each of the plurality of samples to be detected being the specific base at the interested locus, further updating, by using each new expected value, the initial frequency of the sequencing data of the plurality of samples to be detected being the specific base at the interested locus, and repeating the foregoing iteration until the expected value of each of the plurality of samples to be detected being the specific base at the interested locus converges; and determining, based on each converging expected value, a base mutation type and a mutation confidence at the interested locus of each of the plurality of samples to be detected. The specific base includes an adenine A base, a thymine T base, a cytosine C base, or a guanine G base.

The embodiments of the present disclosure further disclose a base mutation detection apparatus based on sequencing data, including: an initial frequency determination module configured to determine an initial frequency of an initial frequency of sequencing data of a plurality of samples to be detected being a specific base at an interested locus; an expected value calculation module configured to calculate, based on the initial frequency, an expected value of each of the plurality of samples to be detected being the specific base at the interested locus; an update module configured to update, by using each expected value, the initial frequency of the sequencing data of the plurality of samples to be detected being the specific base at the interested locus; an iteration module configured to: further calculate, by using the updated initial frequency, the expected value of each of the plurality of samples to be detected being the specific base at the interested locus, further update, by using each new expected value, the initial frequency of the sequencing data of the plurality of samples to be detected being the specific base at the interested locus, and repeat the foregoing iteration until the expected value of each of the plurality of samples to be detected being the specific base at the interested locus converges; and a mutation type determination module configured to determine, based on each converging expected value, a base mutation type and a mutation confidence at the interested locus of each of the plurality of samples to be detected. The specific base includes adenine A base, thymine T base, cytosine C base, or guanine G base.

Embodiments of the present disclosure further disclose a storage medium including a computer-executable instruction. The computer-executable instruction, when executed by a computer processor, implements the aforementioned base mutation detection method based on sequencing data.

The base mutation detection method based on sequencing data disclosed in the embodiments of the present disclosure can achieve the base mutation detection for a large amount of sequencing data with low sequencing depth, by means of determining an initial frequency of sequencing data of a plurality of samples to be detected being a specific base at an interested locus; calculating, based on the initial frequency, an expected value of each of the plurality of samples to be detected being the specific base at the interested locus; updating, by using each expected value, the initial frequency of the sequencing data of the plurality of samples to be detected being the specific base at the interested locus; further calculating, by using the updated initial frequency, the expected value of each of the plurality of samples to be detected being the specific base at the interested locus, further updating, by using each new expected value, the initial frequency of the sequencing data of the plurality of samples to be detected being the specific base at the interested locus, and repeating the foregoing iteration until the expected value of each of the plurality of samples to be detected being the specific base at the interested locus converges; determining, based on each converging expected value, a base mutation type and a mutation confidence at the interested locus of each of the plurality of samples to be detected.

DESCRIPTION OF EMBODIMENTS

The following is an overview of the subjects described herein. This overview is not intended to limit the protection scope of the claims.

Unless otherwise defined, all technical and scientific terms used herein have the common meanings that can be understood by those skilled in the art. The terminology used herein is intended to describe specific embodiments and is not used to limit the present disclosure. The term "and/or" as used herein includes any and all combinations of one or more listed items.

The base mutation detection method based on sequencing data disclosed in the embodiments of the present disclosure can be applied to prenatal testing or other ultra-large-scale population sequencing data, the sequencing depth of which is usually low. The base mutation detection method based on sequencing data provided in the present disclosure can also be used in situations of greater sequencing depth. Although the sequencing depth of each sample is very low, each site is covered by many multiplying base sequences (hereinafter referred to as reads) when the samples are in a great number. Each base derived from an independent read and covering the current site shall correspond to a base quality score generated by the sequencer. The base quality score is recorded as $p(d_i|b_{i,j})$, which specifically represents a quality score of a base j, which is derived from an independent read $d_i$ from a sample i and covers the current site. The base quality score reflects a detection error probability of the corresponding base. For example, the base covered by a first read in a first locus L1={A,T} is one base A, and a base quality score of A is 30, which means that a detection error probability of base A at the first locus of the first read is $10^{-(30/10)}=10^{-3}$, and the corresponding correct probability is $1-10^{-3}$, where A represents an adenine base, T represents a thymine base, and C represents a cytosine base, and G represents a guanine base. If the sample is a prenatal sample and the current site is covered by more than one reads, only one read sequence is drawn from each sample, in order to avoid the problem that these reads are not independent due to the mixing of fetal and maternal DNAs.

Figure 1:
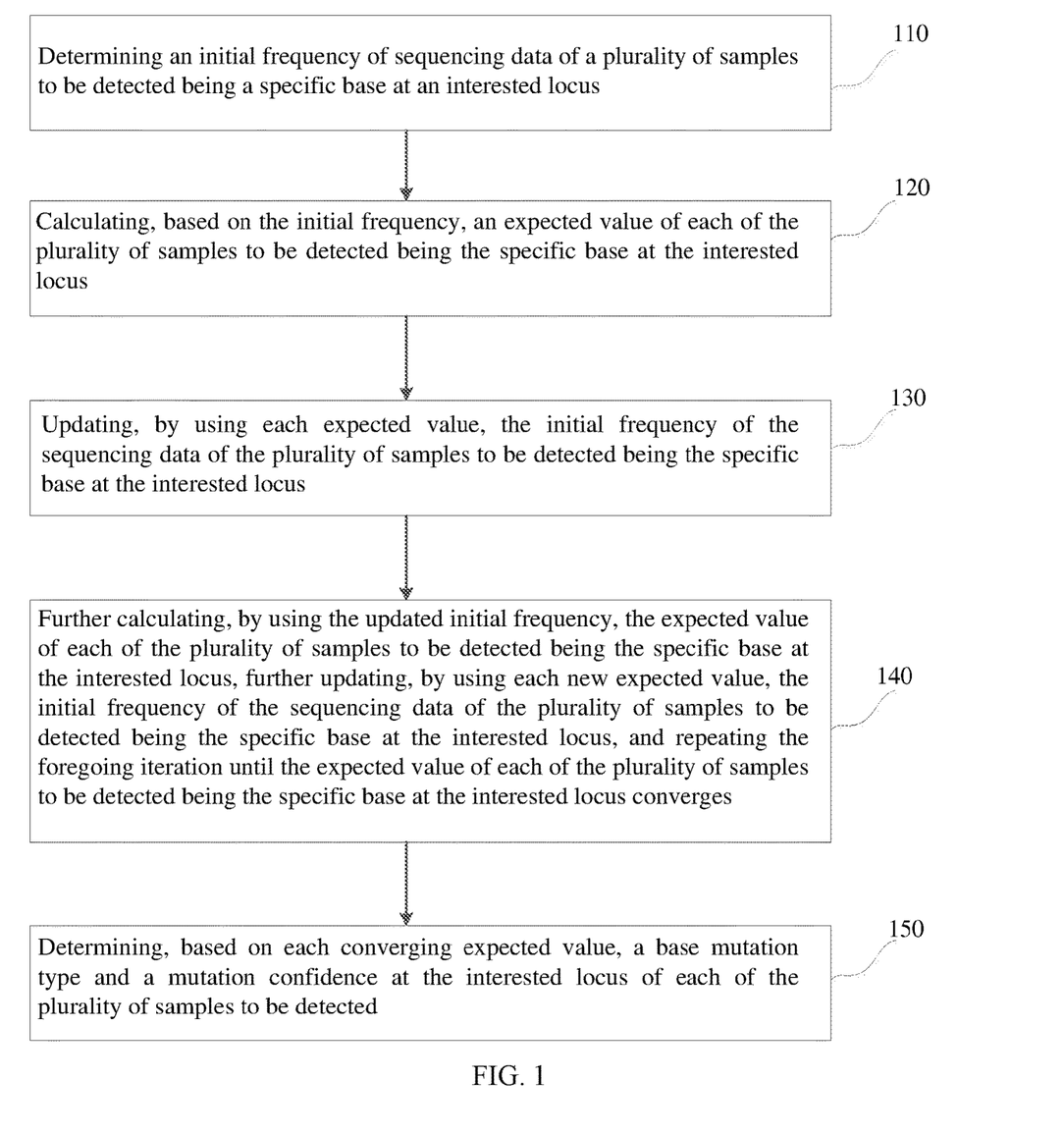
FIG. 1 is a schematic flow chart of a base mutation detection method based on sequencing data according to an embodiment of the present disclosure.

FIG. 1 is a schematic flow chart of a base mutation detection method based on sequencing data according to an embodiment of the present disclosure. As shown in FIG. 1, the method includes the following steps.

In step 110, determined is an initial frequency of a specific base at an interested locus in sequencing data of a plurality of samples to be detected.

The interested locus refers to a position to be detected whether a base mutation occurs. The specific base includes an adenine (A) base, a thymine (T) base, a cytosine (C) base, or a guanine (G) base.

In one embodiment, said determining the initial frequency of a specific base at an interested locus in sequencing data of the plurality of samples to be detected: statistically calculating the number of the specific base in the sequencing data of the plurality of samples to be detected and the total number of bases of four types in the sequencing data of the plurality of samples to be detected; and determining a quotient of dividing the number of the specific base by the total number of the bases of four types as the initial frequency of the specific base at the interested locus based on the sequencing data of the plurality of samples to be detected.

The above-mentioned process of determining the initial frequency is expressed by an equation:

$$p_j = \frac{\sum_{i=1}^{N} b_{ij}}{n} \quad (1)$$

where $b_{ij}$ represents the number of specific bases j carried in the sequencing data of a sample i to be detected; N represents the total number of samples to be detected;

$$\sum_{i=1}^{N} b_{ij}$$

represents the total number of specific base j carried in the sequencing data of the plurality of samples to be detected; n represents the total number of bases of the four types in the sequencing data of the plurality of samples to be detected; $p_j$ represents the initial frequency of the sequencing data of the plurality of samples to be detected being the specific base j at the interested locus, j={0,1,2,3}; $p_O$ Represents the Initial Frequency of the Sequencing Data of the plurality of samples to be detected being the base A at the interested locus; $p_1$ represents the initial frequency of the sequencing data of the plurality of samples to be detected being the base C at the interested locus; $p_2$ represents the initial frequency of the sequencing data of the plurality of samples to be detected being the base G at the interested locus; and $p_3$ represents the initial frequency of the sequencing data of the plurality of samples to be detected being the base T at the interested locus.

In step 120, calculated is an expected value of each sample to be detected being the specific base at the interested locus, based on the initial frequency.

In one embodiment, the expected value of the case that each sample to be detected has the specific base at the interested locus is calculated in accordance with the following equation (2):

$$p(b_{i,j}|p_j, d_i) = \frac{p(b_{i,j}|p_j)p(d_i|b_{i,j})}{\sum_{b_{i,j}=0}^{3} p(b_{i,j}|p_j)p(d_i|b_{i,j})} \quad (2)$$

where $b_{i,j}$ represents that a sample i to be detected is a specific base j at an interested locus; $p_j$ represents an initial frequency of the sequencing data of the plurality of samples to be detected being the specific base j at the interested locus; $d_i$ represents a set of bases in base sequences at the interested locus covered by the sample i to be detected; $p(b_{i,j}|p_j,d_i)$ represents an expected value of the sample i to be detected being the specific base j at the interested locus; $p(b_{i,j}|p_j)$ represents a prior probability of the sample i to be detected being the specific base j at the interested locus under a given $p_j$; and $p(d_i|b_{i,j})$ represents a base quality score of base sequences at the interested locus covered by the sample i to be detected.

In step 130, by using each expected value, the initial frequency of the sequencing data of the plurality of samples to be detected being the specific base at the interested locus is updated.

In an embodiment, the initial frequency of the sequencing data of the plurality of samples to be detected being the specific base at the interested locus is updated by using each expected value in accordance with the following equation (3):

$$\hat{p}_j = \frac{\sum_{i=1}^{N} p(b_{i,j}|p_j, d_i)}{n} \quad (3)$$

where $\hat{p}_j$ represents an updated initial frequency of the sequencing data of the plurality of samples to be detected being the specific base at the interested locus; $p(b_{i,j}|p_j,d_i)$ represents an expected value of the sample i to be detected being the specific base j at the interested locus; N represents the number of the plurality of samples to be detected; and n represents the total number of bases of four types in the sequencing data of the plurality of samples to be detected. The bases of four types refer to bases A, T, C, and G.

In step 140, the expected value of each of the plurality of samples to be detected being the specific base at the interested locus is further calculated by using the updated initial frequency; the initial frequency of the sequencing data of the plurality of samples to be detected being the specific base at the interested locus is further updated by using each new expected value; and the foregoing iteration is repeated until the expected value of each of the plurality of samples to be detected being the specific base at the interested locus converges.

In an embodiment, the result $\hat{p}_j$ derived from the above equation (3) is used to replace $p_j$ in the equation (2), such that the new expected value of each sample to be detected being the specific base at the interested locus is derived from the equation (2). The new expected value is used to further update the initial frequency of the sequencing data of the plurality of samples to be detected being the specific base at the interested locus based on the above equation (3), until the expected value derived from the equation (2) converges. The conditions for convergence of the expected value include: a difference between the expected values obtained in successive iterations is smaller than one ten thousandth for three consecutive times. For example, the expected value obtained from the 10-th iteration is q10, the expected value obtained from the 11-th iteration is q11, and the expected value obtained in the 12-th iteration is q12, and the expected value obtained in the 13-th iteration is q13; when (q11−q10) <0.0001, (q12−q11)<0.0001, and (q13-q12)<0.0001, it can be determined that the expected value meets the conditions for convergence, and the expected value q13 is the converging expected value.

The optimal base frequency cannot be obtained until the expected value converges, that is, the optimal base frequency is a value of the above equation (3) corresponding to the convergence of the expected value, i.e., the frequency of the interested locus being the specific base j.

In step 150, a base mutation type and a mutation confidence at the interested locus of each sample to be detected are determined based on each converging expected value.

In an embodiment, said determining, based on each converging expected value, the base mutation type and the mutation confidence at the interested locus of each of the plurality of samples to be detected includes: calculating, based on each converging expected value, a maximum likelihood estimate of the plurality of samples to be detected belonging to each one of four specific base mutation types at the interested locus; calculating a ratio of the maximum likelihood estimates of two adjacent specific base mutation types; processing the ratio according to a preset rule to obtain a probability corresponding to the ratio; and determining the specific base mutation type at the interested locus of each sample to be detected as the specific base mutation type corresponding to a current denominator, when the probability is smaller than a set threshold. The four specific base mutation types comprise mono-allelic mutation, bi-allelic mutation, tri-allelic mutation, and tetra-allelic mutation.

Said calculating, based on each converging expected value, the maximum likelihood estimate of the plurality of samples to be detected belonging to each one of four specific base mutation types at the interested locus includes: calculating the maximum likelihood estimate of the plurality of samples to be detected belonging to each one of four specific base mutation types at the interested locus in accordance with the following equation (4):

$$p(D|p_j) = \prod_{i=1}^{N} \sum_{j=0}^{3} [p(b_{i,j}|p_j)p(d_i|b_{i,j})] \quad (4)$$

where D represents observation data composed of sets of bases in base sequences at the interested locus covered by all of the plurality of to be detected; $p_j$ represents a frequency of the sequencing data of the plurality of samples to be detected being a specific base j at the interested locus, which is obtained based on each converging expected value; $p(D|p_j)$ represents a maximum likelihood estimate of the plurality of samples to be detected being a base mutation type corresponding to j at the interested locus; $p(b_{i,j}|p_j)$ represents a prior probability of the sample i to be detected being the specific base j at the interested locus under a given $p_j$; and $p(d_i|b_{i,j})$ represents abase quality score of abase sequence at the interested locus covered by the sample i; when j=0, the specific base mutation type corresponding to j is the mono-allelic mutation; when j=1, the specific base mutation type corresponding to j is the bi-allelic mutation; when j=2, the specific base mutation type corresponding to j is the tri-allelic mutation; and when j=3, the specific base mutation type corresponding to j is the tetra-allelic mutation.

In an embodiment, said calculating the ratio of the maximum likelihood estimates of the two adjacent specific base mutation types includes: assuming that a maximum likelihood estimate of the interested locus being the tetra-allelic mutation is $f_4$, and a maximum likelihood estimate of the interested locus being the tri-allelic mutation is $f_3$; and determining $$\frac{f_3}{f_4}$$

as the ratio of the maximum likelihood estimates of the two adjacent specific base mutation types.

Assuming that a maximum likelihood estimate of the interested locus being the bi-allelic mutation is $f_2$, and a minimum value of maximum likelihood estimates of four mutation combinations in the tri-allelic mutations is $f_3$ min; the four mutation combinations of the tri-allelic mutation are {A,T,C}, {A,T,G}, {T,C,G}, and {A,C,G}, respectively, and each mutation combination corresponds to one maximum likelihood estimate described in the above equation (4). Thus, $$\frac{f_2}{f_3 \text{ min}}$$

is determined as the ratio of the maximum likelihood estimates of the two adjacent specific base mutation types.

Assuming that a maximum likelihood estimate of the interested locus being a mono-allelic mutation is $f_1$, and a minimum value of maximum likelihood estimates of 16 mutation combinations in the bi-allelic mutations is $f_2$ min then $$\frac{f_1}{f_2 \text{ min}}$$

is determined as the ratio of the maximum likelihood estimates of the two adjacent specific base mutation types.

Correspondingly, said processing the ratio according to the preset rule to obtain the probability corresponding to the ratio includes: calculating a natural logarithm of the ratio to obtain a first result; multiplying the obtained first result by −2 to obtain a second result; and obtaining a probability corresponding to the second result by looking up the chi-square distribution table.

The mutation frequency of any one base is assumed to be 0 in the case of tri-allelic mutation, the mutation frequency of any two bases in the case of bi-allelic mutation is assumed to be 0, and the mutation frequency of any three bases in the case of mono-allelic mutation is assumed to be 0. In this regard, the numerator of each of the above fractions $$\left(\frac{f_3}{f_4}, \frac{f_2}{f_3 \text{ min}}\right)$$

and $$\frac{f_1}{f_2 \text{ min}}\right)$$

is smaller than the denominator by a frequency parameter $P_j$. Therefore, the statistic, which is obtained by calculating the natural logarithm of the above ratio and multiplying the natural logarithm by −2, obeys a chi-square distribution with one degree of freedom. Thus, the probability corresponding to each ratio can be obtained by using the chi-square distribution table.

The statistic obtained by calculating the natural logarithm of the above ratio and multiplying the natural logarithm by −2 is as follows:

$$LRT_{4vs3} = -2\ln\left(\frac{f_3}{f_4}\right)$$

$$LRT_{3vs2} = -2\ln\left(\frac{f_2}{f_3 \text{ min}}\right)$$

$$LRT_{2vs1} = -2\ln\left(\frac{f_1}{f_2 \text{ min}}\right)$$

When the probability is smaller than the set threshold, for example, when the LRT probability corresponding to $LRT_{4vs3}$ is smaller than $10^{-6}$, it is determined that the assumption is not true, i.e., it is determined that the interested locus does not belong to the tri-allelic mutation, but belonging to the tetra-allelic mutation. When the probability corresponding to $LRT_{3vs2}$ is smaller than $10^{-6}$, it is determined that the interested locus does not belong to the bi-allelic mutation, but belonging to the tri-allelic mutation. When the probability corresponding to $LRT_{2vs1}$ is smaller than $10^{-6}$, it is determined that the interested locus does not belong to the mono-allelic mutation, but belonging to the bi-allelic mutation.

In an embodiment, said determining, based on each converging expected value, the mutation confidence at the interested locus of each sample to be detected includes: performing a regular Phred-scale transformation on the probability corresponding to $$\frac{f_1}{f_2 \text{ min}}$$

to obtain a Phred quality score; and determining the Phred quality score as the mutation confidence at the interested locus of each sample to be detected.

The mutation confidence can be used to further determine whether the base mutation at the interested locus is true.

The embodiments of the present disclosure disclose a base mutation detection method based on sequencing data, which is completely different from the mutation detection method known in related art, and has significant advantages in time complexity. By utilizing the data characteristics of a large amount of sample data and low sequencing depth of individual sample, the likelihood function method of observing the data based on allelic mutation types is directly used, instead of using the likelihood function of observing the data based on the genotype. In this way, the whole detection method is faster and more efficient, and enables the analysis of more than 100,000 or even one million samples (for example, one million cases of prenatal testing data). In addition, in the embodiments of the present disclosure, instead of presupposing that the interested locus is a bi-allelic mutation, for the first time, a plurality of likelihood tests are used to test the maximum likelihood estimates of different base combinations. Therefore, the base mutation detection method of the embodiments of the present disclosure has the capability of detecting bi-allelic mutations, as well as mono-allelic and multi-allelic mutations. When the base mutation detection method of the embodiments of the present disclosure is used to analyze the prenatal testing data of one hundred thousand or one million cases, high-precision population mutation position and frequency information can be obtained, and such information has both scientific research and industrial values.

Figure 2:
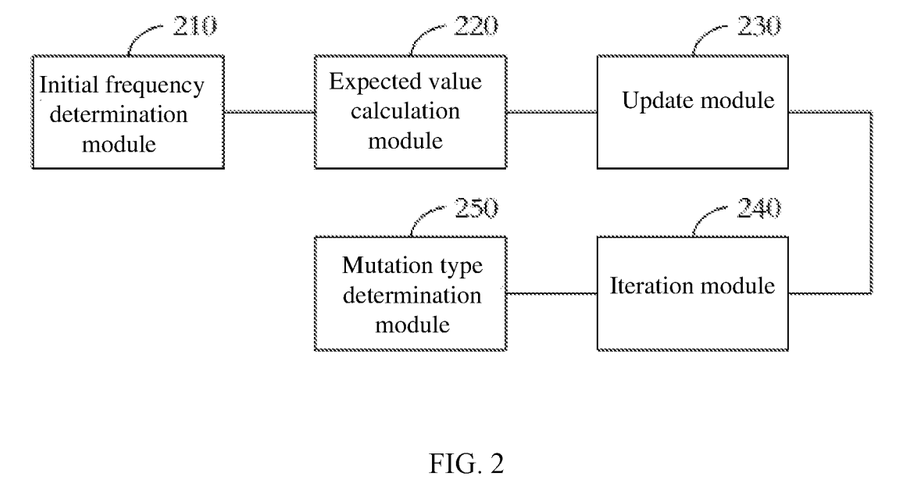
FIG. 2 is a schematic structural diagram of a base mutation detection apparatus based on sequencing data according to an embodiment of the present disclosure.

FIG. 2 is a schematic structural diagram of a base mutation detection apparatus based on sequencing data according to an embodiment of the present disclosure. As shown in FIG. 2, the device includes an initial frequency determination module 210, an expected value calculation module 220, an update module 230, an iteration module 240, and a mutation type determination module 250.

In this embodiment, the initial frequency determination module 210 is configured to determine an initial frequency of an initial frequency of sequencing data of a plurality of samples to be detected being a specific base at an interested locus; the expected value calculation module 220 is configured to calculate, based on the initial frequency, an expected value of each of the plurality of samples to be detected being the specific base at the interested locus; the update module 230 is configured to update, by using each expected value, the initial frequency of the sequencing data of the plurality of samples to be detected being the specific base at the interested locus; the iteration module 240 is configured to further calculate, by using the updated initial frequency, the expected value of each of the plurality of samples to be detected being the specific base at the interested locus, further update, by using each new expected value, the initial frequency of the sequencing data of the plurality of samples to be detected being the specific base at the interested locus, and repeat the foregoing iteration until the expected value of each of the plurality of samples to be detected being the specific base at the interested locus converges; the mutation type determination module 250 is configured to determine, based on each converging expected value, a base mutation type and a mutation confidence at the interested locus of each of the plurality of samples to be detected. The specific base includes adenine Abase, thymine T base, cytosine C base, or guanine G base.

The base mutation detection apparatus based on sequencing data disclosed in the embodiment of the present disclosure can achieve the base mutation detection for a large amount of sequencing data with low sequencing depth, by means of determining an initial frequency of sequencing data of a plurality of samples to be detected being a specific base at an interested locus; calculating, based on the initial frequency, an expected value of each of the plurality of samples to be detected being the specific base at the interested locus; updating, by using each expected value, the initial frequency of the sequencing data of the plurality of samples to be detected being the specific base at the interested locus; further calculating, by using the updated initial frequency, the expected value of each of the plurality of samples to be detected being the specific base at the interested locus, further updating, by using each new expected value, the initial frequency of the sequencing data of the plurality of samples to be detected being the specific base at the interested locus, and repeating the foregoing iteration until the expected value of each of the plurality of samples to be detected being the specific base at the interested locus converges; determining, based on each converging expected value, a base mutation type and a mutation confidence at the interested locus of each of the plurality of samples to be detected.

It should be noted that, the specific working principle of each component in the device embodiment can refer to the corresponding part of the method embodiment, which will not be repeated herein.

In an embodiment, in order to verify the effect of the above-mentioned base mutation detection method, an example of analysis using the above-mentioned base mutation detection method is now provided. In this example, the above-mentioned base mutation detection method is used to analyze large-scale simulation data, in order to test the mutation recall, false positive rate, and difference between the estimated and true values of the mutation position frequency of the above-mentioned base mutation detection method.

Example

Simulation Data Overview

The simulation data simulates a total of 100 monopolymic loci, 50,000 di-allelic loci, 50,000 tri-allelic loci, and 50,000 tetra-allelic loci. For each of the above three groups of 50,000 loci, the minimum allelic mutation frequency is set at an interval of $1/10,000$ of the loci, for example, as shown in Table 1:

TABLE 1

| | Mutation frequency distribution of simulation data | | | | |
|---|---|---|---|---|---|
| Allele locus | Mutation frequency (A) | Mutation frequency (C) | Mutation frequency (G) | Mutation frequency (T) | Allele type |
| 1 | 1 | 0 | 0 | 0 | 1 |
| 2 | 1 | 0 | 0 | 0 | 1 |

TABLE 1-continued

Mutation frequency distribution of simulation data

| Allele locus | Mutation frequency (A) | Mutation frequency (C) | Mutation frequency (G) | Mutation frequency (T) | Allele type |
|---|---|---|---|---|---|
| 3 | 1 | 0 | 0 | 0 | 1 |
| ... | | | | | |
| 98 | 1 | 0 | 0 | 0 | 1 |
| 99 | 1 | 0 | 0 | 0 | 1 |
| 100 | 1 | 0 | 0 | 0 | 1 |
| 101 | 1.00E−05 | 0.99999 | 0 | 0 | 2 |
| 102 | 2.00E−05 | 0.99998 | 0 | 0 | 2 |
| 103 | 3.00E−05 | 0.99997 | 0 | 0 | 2 |
| ... | | | | | |
| 50098 | 0.49998 | 0.50002 | 0 | 0 | 2 |
| 50099 | 0.49999 | 0.50001 | 0 | 0 | 2 |
| 50100 | 0.5 | 0.5 | 0 | 0 | 2 |
| ... | | | | | |
| 50101 | 1.00E−05 | 0.499995 | 0.499995 | 0 | 3 |
| 50102 | 2.00E−05 | 0.49999 | 0.49999 | 0 | 3 |
| 50103 | 3.00E−05 | 0.499985 | 0.499985 | 0 | 3 |
| 100098 | 0.49998 | 0.25001 | 0.25001 | 0 | 3 |
| 100099 | 0.49999 | 0.250005 | 0.250005 | 0 | 3 |
| 100100 | 0.5 | 0.25 | 0.25 | 0 | 3 |
| ... | | | | | |
| 100101 | 1.00E−05 | 0.33333 | 0.33333 | 0.33333 | 4 |
| 100102 | 2.00E−05 | 0.333326667 | 0.333326667 | 0.333326667 | 4 |
| 100103 | 3.00E−05 | 0.333323333 | 0.333323333 | 0.333323333 | 4 |
| 150098 | 0.49998 | 0.166673333 | 0.166673333 | 0.166673333 | 4 |
| 150099 | 0.49999 | 0.16667 | 0.16667 | 0.16667 | 4 |
| 150100 | 0.5 | 0.166666667 | 0.166666667 | 0.166666667 | 4 |

Figure 3:
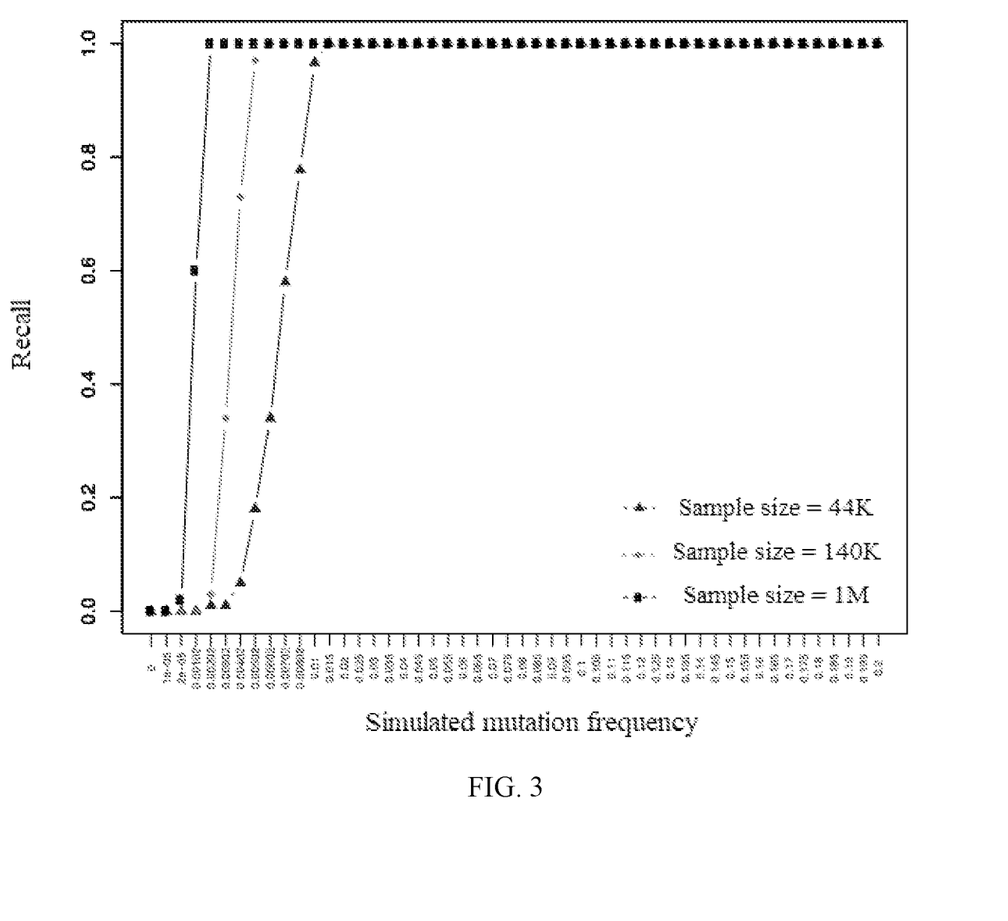
FIG. 3 is a schematic diagram illustrating recalls of different mutation frequencies with different sample data by using the above-mentioned base mutation detection method according to an embodiment of the present disclosure.

After setting the base mutation frequency distribution as illustrated in Table 1, the sample sequencing depth is set to be 0.06×, and the sequencing error rate is set to be about 0.01. The main purpose of the simulation data is to observe the mutation recall, the false positive rate, and the difference between the estimated and true values of the mutation locus frequency of the above-mentioned base mutation detection method based on sequencing data provided in the embodiments of the present disclosure under different conditions (different sample sizes, different mutation frequencies, and different mutation types). FIG. 3 is a schematic diagram of recalls of different mutation frequencies by using the above-mentioned base mutation detection method with different sample data according to an embodiment of the present disclosure, where the horizontal axis represents the mutation frequency, and the vertical axis represents the recall. FIG. 3 illustrates the recalls of sample sizes of 44,000 (44 k) people, 140,000 (140 k) people, and 1 million (1 M) people under different mutation frequencies. Under a certain sample size, the minimum mutation frequency that the above-mentioned sequencing data-based base mutation detection method can detect (when the recall is greater than 0) and the minimum mutation frequency when the recall reaches 100% usually receive attention from the investigators. It can be seen from FIG. 3 that, with the increase of the sample size from 44 k to 140 k to 1 M, the minimum mutation frequencies detected when the recall is greater than 0 are 0.002, 0.001, and 0.00002, respectively, and the minimum mutation frequencies when the recall reaches 100% (full detection mutation frequencies) are 0.015, 0.005, and 0.002, respectively, revealing the good performances of the above-mentioned base mutation detection method based on sequencing data. In particular, none of the mutation of the 100 monopolymic loci is falsely detected, i.e., the false positive rate is zero. The results shown in FIG. 3 indicate that the base mutation detection method based on sequencing data provided in the embodiments of the present disclosure can sensitively and accurately detect mono-allelic mutations from a large amount of sequencing data with a depth as low as 0.06×.

Figure 4:
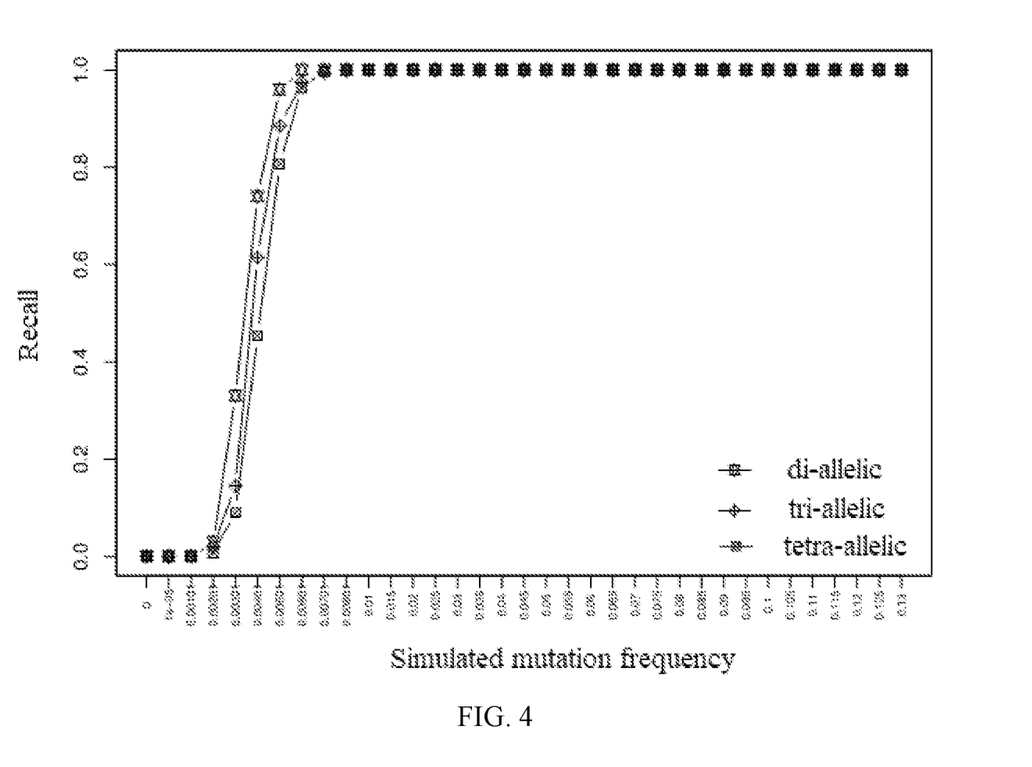
FIG. 4 is a schematic diagram illustrating recall of different mutation types under different mutation frequencies by using the above-mentioned base mutation detection method according to an embodiment of the present disclosure, where the number of samples is 140,000.

FIG. 4 is a schematic diagram of mutation recalls of different mutation types by using the above-mentioned base mutation detection method under different mutation frequencies when the sample size is 140,000, where the horizontal axis represents the mutation frequency, and the vertical axis represents the recall. It can be seen from FIG. 4 that, for the bi-allelic mutation, the minimum mutation frequency that can be detected (when the recall is greater than 0) and the minimum mutation frequency when the recall reaches 100% are 0.002 and 0.005, respectively. Although the recalls of the relatively difficult tri-allelic mutations and tetra-allelic mutations are slightly lower than that of the bi-allelic mutations, the difference in effect is insignificant. For the tri-allelic mutations, the minimum mutation frequency that can be detected (when the recall is greater than 0) and the lowest mutation frequency when the recall reaches 100% are 0.002 and 0.008, respectively. For the tetra-allelic mutations, the minimum mutation frequency that can be detected (when the recall is greater than 0) and the lowest mutation frequency when the recall reaches 100% are 0.001 and 0.008, respectively. Similarly, none of the non-mutation sites is detected, which reflects the high accuracy of the method. The results shown in FIG. 4 demonstrate that the base mutation detection method based on sequencing data provided by the embodiments of the present disclosure can detect the tri-allelic or tetra-allelic mutations sensitively and accurately.

Figure 5:
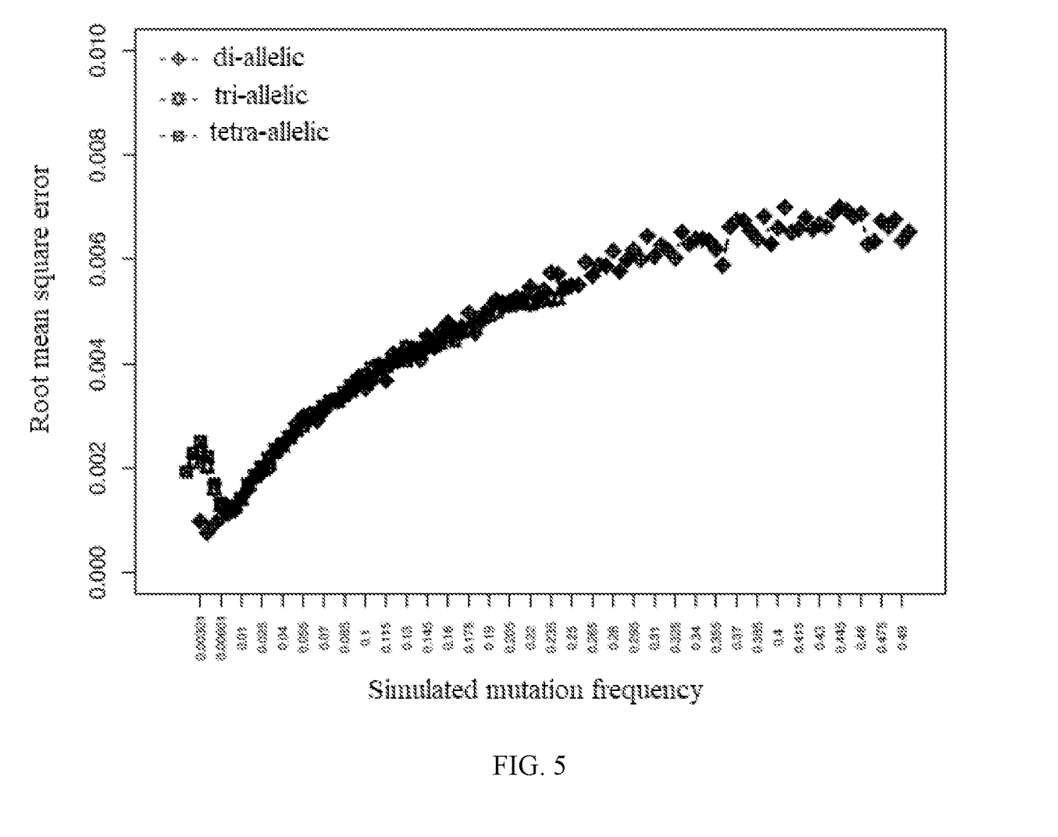
FIG. 5 is a schematic diagram illustrating differences between true and estimated values of mutation frequency of a mutation site under different mutation frequencies by using the above-mentioned base mutation detection method according to an embodiment of the present disclosure.
Figure 6:
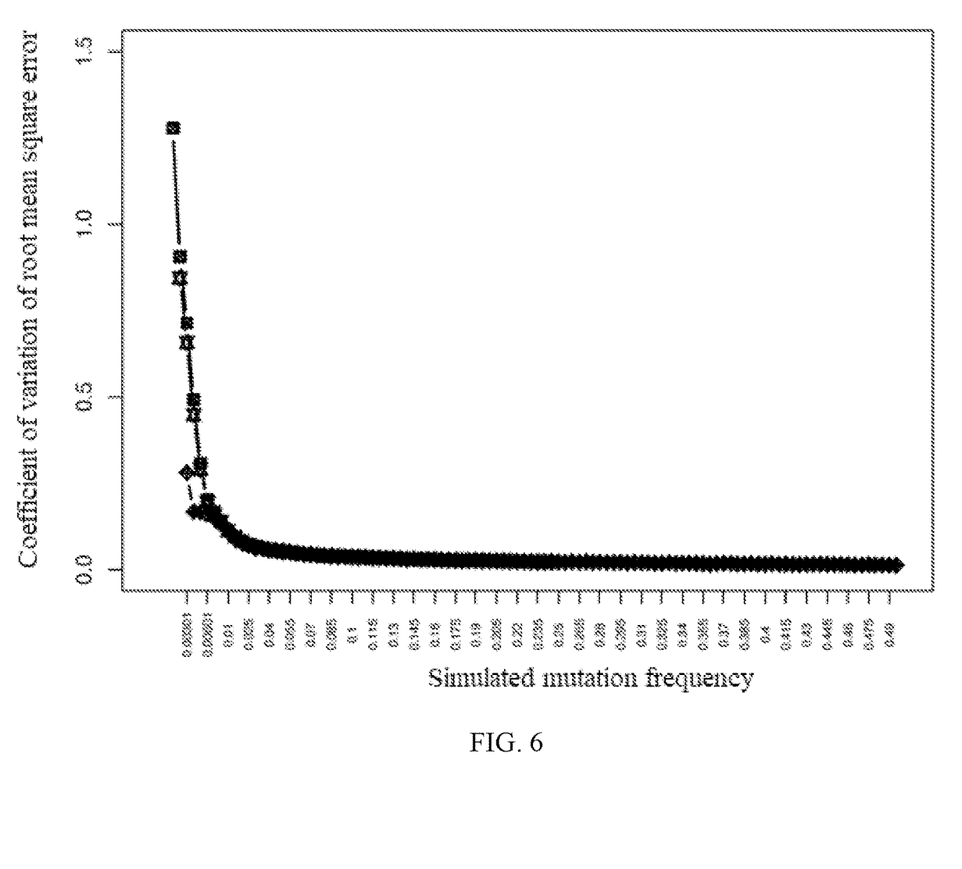
FIG. 6 is a schematic diagram illustrating differences between true and estimated values of mutation frequency of a mutation site under different mutation frequencies by using the above-mentioned base mutation detection method according to another embodiment of the present disclosure.

FIG. 5 and FIG. 6 are schematic diagrams illustrating differences between the estimated and true values of the mutation frequency of the mutation position by using the above-mentioned base mutation detection method under different mutation frequencies, where the horizontal axis represents the mutation frequency, the vertical axis of FIG. 5 represents the root-mean-square error, and the vertical axis of FIG. 6 represents the coefficient of variation of the root mean square error. FIG. 5 reflects an average difference between a frequency of each frequency band and a true mutation frequency, which intuitively reflects the approximate difference between the detected frequency and the true frequency, but fails to allow a transverse comparison of the different frequencies due to different measures of different frequency bands. In FIG. 6, the measures of different frequency bands are unified, such that the frequency detected by the method and the true frequency can be compared under different frequency bands to evaluate the difference therebetween. It can be seen from FIG. 5 that, with the increase of the simulated mutation frequency, the detected frequency is slightly different from the real frequency. It can be seen from FIG. 6 that a measure difference of the low-frequency frequency (<0.003) and the real frequency band is about 1 fold to 1.5 folds, and the mutation with a frequency greater than 0.003 is smaller than the measure difference. Through this analysis, it can be seen that the above method can accurately detect the true mutation frequency for the detected mutation position.

An embodiment of the present disclosure further provides a storage medium containing a computer-executable instruction, and the computer-executable instruction, when executed by a computer processor, implements a base mutation detection method based on sequencing data. The method includes: determining an initial frequency of sequencing data of a plurality of samples to be detected being a specific base at an interested locus; calculating, based on the initial frequency, an expected value of each of the plurality of samples to be detected being the specific base at the interested locus; updating, by using each expected value, the initial frequency of the sequencing data of the plurality of samples to be detected being the specific base at the interested locus; further calculating, by using the updated initial frequency, the expected value of each of the plurality of samples to be detected being the specific base at the interested locus, further updating, by using each new expected value, the initial frequency of the sequencing data of the plurality of samples to be detected being the specific base at the interested locus, and repeating the foregoing iteration until the expected value of each of the plurality of samples to be detected being the specific base at the interested locus converges; and determining, based on each converging expected value, a base mutation type and a mutation confidence at the interested locus of each of the plurality of samples to be detected. The specific base comprises an adenine A base, a thymine T base, a cytosine C base, or a guanine G base.

It should be noted that relational terms such as "first" and "second" in the present disclosure are only used to distinguish one entity or operation from another entity or operation, and do not necessarily require or imply the presence of any such actual relationship or sequence of these entities or operations. Moreover, the term "include", "comprise", "contain", or any other variants thereof means a non-exclusive inclusion. Thus, a process, method, article or device, which is described to include a series of elements, not only includes the mentioned elements, but also includes other elements that are not explicitly listed, or further include elements inherent to the process, method, article or device. Without more restrictions, an element defined by the expression "including a . . . ", "comprising a . . . " does not exclude the presence of other identical elements in the process, method, article, or device that includes the element.

The foregoing description of the disclosed embodiments enables those skilled in the art to implement or use the present disclosure.

What is claimed is:

1. A base mutation detection method based on sequencing data, the base mutation detection method comprising:
   determining an initial frequency of sequencing data of a plurality of samples to be detected being a specific base at an interested locus;
   calculating, based on the initial frequency, an expected value of each of the plurality of samples to be detected being the specific base at the interested locus;
   updating, by using each expected value, the initial frequency of the sequencing data of the plurality of samples to be detected being the specific base at the interested locus;
   further calculating, by using the updated initial frequency, the expected value of each of the plurality of samples to be detected being the specific base at the interested locus, further updating, by using each new expected value, the initial frequency of the sequencing data of the plurality of samples to be detected being the specific base at the interested locus, and repeating the foregoing iteration until the expected value of each of the plurality of samples to be detected being the specific base at the interested locus converges; and
   determining, based on each converging expected value, a base mutation type and a mutation confidence at the interested locus of each of the plurality of samples to be detected,
   wherein the specific base comprises an adenine A base, a thymine T base, a cytosine C base, or a guanine G base.

2. The method according to claim 1, wherein said determining the initial frequency of the sequencing data of a plurality of samples to be detected being the specific base at the interested locus comprises:
   statistically calculating the number of the specific base in the sequencing data of the plurality of samples to be detected and the total number of bases of four types in the sequencing data of the plurality of samples to be detected, wherein the bases of four types comprises the adenine A bases, the thymine T bases, the cytosine C bases, and the guanine G bases; and
   determining a quotient of dividing the number of the specific base by the total number of the bases of four types as the initial frequency of the sequencing data of the plurality of samples to be detected being the specific base at the interested locus.

3. The method according to claim 1, wherein said calculating, based on the initial frequency, the expected value of each of the plurality of samples to be detected being the specific base at the interested locus comprises:
   calculating the expected value of each of the plurality of samples to be detected being the specific base at the interested locus in accordance with the following equation:

$$p(b_{i,j} \mid p_j, d_i) = \frac{p(b_{i,j} \mid p_j)p(d_i \mid b_{i,j})}{\sum_{b_{i,j}=0}^{3} p(b_{i,j} \mid p_j)p(d_i \mid b_{i,j})}$$

where $b_{i,j}$ represents that a sample i to be detected is a specific base j at an interested locus; $p_j$ represents an initial frequency of the sequencing data of the plurality of samples to be detected being the specific base j at the interested locus; $d_i$ represents a set of bases in base sequences at the interested locus covered by the sample i to be detected; $p(b_{i,j}|p_j,d_i)$ represents an expected value of the sample i to be detected being the specific base j at the interested locus; $p(b_{i,j}|p_j)$ represents a prior probability of the sample i to be detected being the specific base j at the interested locus under a given $p_j$; and $p(d_i|b_{i,j})$ represents a base quality score of the base sequences at the interested locus covered by the sample i to be detected.

4. The method according to claim 3, wherein said updating, by using each expected value, the initial frequency of the sequencing data of the plurality of samples to be detected being the specific base at the interested locus comprises:

updating, by using each expected value, the initial frequency of the sequencing data of the plurality of samples to be detected being the specific base at the interested locus in accordance with the following equation:

$$\hat{p}_j = \frac{\sum_{i=1}^{N} p(b_{i,j} | p_j, d_i)}{n}$$

where $\hat{p}_j$ represents an updated initial frequency of the sequencing data of the plurality of samples to be detected being the specific base at the interested locus; $p(b_{i,j}|p_j,d_i)$ represents an expected value of the sample i to be detected being the specific base j at the interested locus; N represents the number of the plurality of samples to be detected; and n represents the total number of bases of four types in the sequencing data of the plurality of samples to be detected.

5. The method according to claim 1, wherein said determining, based on each converging expected value, the base mutation type and the mutation confidence at the interested locus of each of the plurality of samples to be detected comprises:

calculating, based on each converging expected value, a maximum likelihood estimate of the plurality of samples to be detected belonging to each one of four specific base mutation types at the interested locus;

calculating a ratio of the maximum likelihood estimates of two adjacent specific base mutation types;

processing the ratio according to a preset rule to obtain a probability corresponding to the ratio; and when the probability is smaller than a set threshold, determining the specific base mutation type at the interested locus of each sample to be detected as the specific base mutation type corresponding to a current denominator, wherein the four specific base mutation types comprises mono-allelic mutation, bi-allelic mutation, tri-allelic mutation, and tetra-allelic mutation.

6. The method according to claim 5, wherein said calculating, based on each converging expected value, the maximum likelihood estimate of the plurality of samples to be detected belonging to each one of four specific base mutation types at the interested locus comprises:

calculating the maximum likelihood estimate of the plurality of samples to be detected belonging to each one of four specific base mutation types at the interested locus in accordance with the following equation:

$$p(D | p_j) = \prod_{i=1}^{N} \sum_{j=0}^{3} [p(b_{i,j} | p_j) p(d_i | b_{i,j})]$$

where D represents observation data composed of sets of bases in base sequences at the interested locus covered by all of the plurality of samples to be detected; $p_j$ represents a frequency of the sequencing data of the plurality of samples to be detected being a specific base j at the interested locus, which is obtained based on each converging expected value; $p(D|p_j)$ represents a maximum likelihood estimate of the plurality of samples to be detected being a base mutation type corresponding to j at the interested locus; $p(b_{i,j}|p_j)$ represents a prior probability of the sample i to be detected being the specific base j at the interested locus under a given $p_j$; and $p(d_i|b_{i,j})$ represents abase quality score of abase sequence at the interested locus covered by the sample i; when j=0, the specific base mutation type corresponding to j is the mono-allelic mutation; when j=1, the specific base mutation type corresponding to j is the bi-allelic mutation; when j=2, the specific base mutation type corresponding to j is the tri-allelic mutation; and when j=3, the specific base mutation type corresponding to j is the tetra-allelic mutation.

7. The method according to claim 6, wherein said calculating the ratio of the maximum likelihood estimates of the two adjacent specific base mutation types comprises:

determining $$\frac{f_3}{f_4}$$

as the ratio of the maximum likelihood estimates of the two adjacent specific base mutation types, provided that a maximum likelihood estimate of the interested locus being the tetra-allelic mutation is $f_4$, and a maximum likelihood estimate of the interested locus being the tri-allelic mutation is $f_3$.

8. The method according to claim 7, wherein said processing the ratio according to the preset rule to obtain the probability corresponding to the ratio comprises:

calculating a natural logarithm of the ratio to obtain a first result;

multiplying the obtained first result by −2 to obtain a second result; and obtaining a probability corresponding to the second result by looking up a chi-square distribution table.

9. The method according to claim 6, wherein said calculating the ratio of the maximum likelihood estimates of the two adjacent specific base mutation types comprises:

determining $$\frac{f_2}{f_3 \min}$$

as the ratio of the maximum likelihood estimates of the two adjacent specific base mutation types, provided that a maximum likelihood estimate of the interested locus being the bi-allelic mutation is $f_2$, and a minimum value of maximum likelihood estimates of four mutation combinations in the tri-allelic mutations is $f_3$ min.

10. The method according to claim 9, wherein said processing the ratio according to the preset rule to obtain the probability corresponding to the ratio comprises:

calculating a natural logarithm of the ratio to obtain a first result;

multiplying the obtained first result by −2 to obtain a second result; and obtaining a probability corresponding to the second result by looking up a chi-square distribution table.

11. The method according to claim 6, wherein said calculating the ratio of the maximum likelihood estimates of the two adjacent specific base mutation types comprises: determining $$\frac{f_1}{f_2 \min}$$

as the ratio of the maximum likelihood estimates of the two adjacent specific base mutation types, provided that a maximum likelihood estimate of the interested locus being the mono-allelic mutation is $f_1$, and a minimum value of maximum likelihood estimates of 16 mutation combinations in the bi-allelic mutations is $f_2$ min.

12. The method according to claim 11, wherein said processing the ratio according to the preset rule to obtain the probability corresponding to the ratio comprises:

calculating a natural logarithm of the ratio to obtain a first result;

multiplying the obtained first result by −2 to obtain a second result; and obtaining a probability corresponding to the second result by looking up a chi-square distribution table.

13. The method according to claim 11, wherein said determining, based on each converging expected value, the mutation confidence at the interested locus of each sample to be detected comprises:

performing a regular Phred-scale transformation on a probability corresponding to $$\frac{f_1}{f_2 \min}$$

to obtain a Phred quality score; and determining the Phred quality score as the mutation confidence at the interested locus of each sample to be detected.

14. A storage medium, comprising a computer-executable instruction, wherein the computer-executable instruction, when executed by a computer processor, implements the base mutation detection method based on sequencing data according to claim 1.

15. A base mutation detection apparatus based on sequencing data, the base mutation detection apparatus comprising:

an initial frequency determination module configured to determine an initial frequency of an initial frequency of sequencing data of a plurality of samples to be detected being a specific base at an interested locus;

an expected value calculation module configured to calculate, based on the initial frequency, an expected value of each of the plurality of samples to be detected being the specific base at the interested locus;

an update module configured to update, by using each expected value, the initial frequency of the sequencing data of the plurality of samples to be detected being the specific base at the interested locus;

an iteration module configured to: further calculate, by using the updated initial frequency, the expected value of each of the plurality of samples to be detected being the specific base at the interested locus, further update, by using each new expected value, the initial frequency of the sequencing data of the plurality of samples to be detected being the specific base at the interested locus, and repeat the foregoing iteration until the expected value of each of the plurality of samples to be detected being the specific base at the interested locus converges; and a mutation type determination module configured to determine, based on each converging expected value, a base mutation type and a mutation confidence at the interested locus of each of the plurality of samples to be detected, wherein the specific base comprises an adenine A base, a thymine T base, a cytosine C base, or a guanine G base.

* * * * *